United States Patent [19]
Griffith

[11] Patent Number: 4,681,954
[45] Date of Patent: Jul. 21, 1987

[54] 7,8,9,10-TETRAHYDRO-6-OXO-6H-DIBENZO(B,D)PYRANYLOXY-PROPANES

[75] Inventor: Ronald C. Griffith, Pittsford Monroe, N.Y.

[73] Assignee: Pennwalt Corporation, Philadelphia, Pa.

[21] Appl. No.: 784,978

[22] Filed: Oct. 7, 1985

[51] Int. Cl.[4] .......................................... C07D 311/08
[52] U.S. Cl. ........................................ 549/280; 549/5
[58] Field of Search ................................... 549/280, 5

[56] References Cited

U.S. PATENT DOCUMENTS

| | | | |
|---|---|---|---|
| 3,649,650 | 3/1972 | Razdan et al. | 549/390 |
| 4,066,667 | 1/1978 | Lee et al. | 549/280 |
| 4,118,559 | 10/1978 | Johnson et al. | 546/256 |
| 4,126,694 | 11/1978 | Razdan et al. | 514/454 |
| 4,126,695 | 11/1978 | Razdan et al. | 514/454 |
| 4,206,225 | 6/1980 | Johnson | 514/228 |
| 4,569,994 | 2/1986 | Griffith | 549/280 |

OTHER PUBLICATIONS

Gesquiere J. C. et al., Ann. Pharmaceutiquies Francasises 40 (3), 251–257 (1982).

*Primary Examiner*—Jane T. Fan

[57] ABSTRACT

Dibenzopyrone derivatives which possess depressant and/or antihypoxia activity are 7,8,9,10-tetrahydro-6-oxo-6H-dibenzo[b,d]pyranyloxy-propanes having the formula (1):

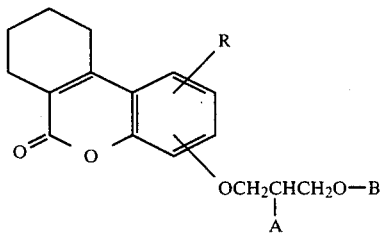

where R represents hydrogen or ($C_1$–$C_4$) alkyl; where A represents chlorine or hydroxyl; and where B represents hydrogen, ($C_1$–$C_4$) alkyl, 7-coumarinyl, phosphono, phenyl, or phenyl substituted with amino, dimethylamino, hydroxyl methoxyl, carboxyl, carboxymethyl, or 2-carboxyethenyl. Also included are pharmaceutically acceptable salts of the compounds.

Compounds of this invention are useful as sedatives or for the protection of warm blooded animals from the effects of oxygen depreviation.

22 Claims, No Drawings

7,8,9,10-TETRAHYDRO-6-OXO-6H-DIBENZO(B,D-)PYRANYLOXY-PROPANES

BACKGROUND OF THE INVENTION

This invention relates generally to 6H-dibenzo[b,d]-pyran-6-one derivatives and more specifically to certain 7,8,9,10-tetrahydro-6-oxo-6H-dibenzo[b,d]pyranyloxypropanes, and pharmaceutically acceptable salt forms, which possess depressant and/or antihypoxia activity.

The compounds of the invention are related to the compounds of applicant's pending application Ser. No. 749,321 filed June 27, 1985 which possess antihypoxia activity.

BRIEF SUMMARY OF THE INVENTION

In accordance with this invention there are provided 7,8,9,10-tetrahydro-6-oxo-6H-dibenzo[b,d]pyranyloxypropanes having the following structural formula (1):

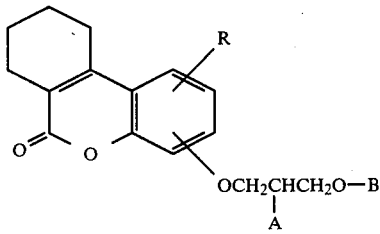

1 where R represents hydrogen or ($C_1$-$C_4$) alkyl; where A represents chlorine or hydroxyl; and where B represents hydrogen, ($C_1$-$C_4$) alkyl, 7-coumarinyl, phosphono, phenyl, or phenyl substituted with amino, dimethylamino, hydroxyl, methoxyl, carboxyl, carboxymethyl, or 2-carboxyethenyl (HOOC—CH=CH—). Pharmaceutically acceptable salts prepared from the compounds of formula 1 which contain acidic or basic functional groups are also included within the scope of the invention.

Compounds of this invention possess depressant properties and/or antihypoxia activity, and are useful as sedatives and/or for the protection of warm blooded animals from the effects of oxygen deprivation.

DETAILED DESCRIPTION OF THE INVENTION

In accordance with the preferred process employed for the preparation of the compounds of this invention where A=hydroxyl and B is other than hydrogen, the readily synthesized (See R. Adams and B. R. Baker, *J. Am. Chem. Soc.*, 1940, 62, 2405 and Preparation of Intermediates Section), 7,8,9,10-tetrahydro-6-oxo-6H-dibenzo[b,d]pyran intermediates of formula 2

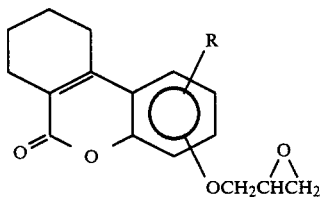

2

(where R is as described above for 1) are reacted with various commercially available alcohols or phenols in an inert solvent in the presence of a base such as sodium hydroxide. For example, reaction of intermediates of formula 2 in the presence of sodium hydroxide with methanol, ethanol, n-propanol, i-propanol, n-butanol, t-butanol, 7-hydroxycoumarin, phenol, 2,3 or 4-methoxyphenyl, 2,3 or 4-carboxyphenol, 2,3 or 4-(carboxymethyl)phenol, 2,3 or 4-aminophenol, 2,3 or 4-(dimethylamino)phenol, 2,3 or 4-hydroxyphenol, or 2,3 or 4-[2-carboxyethenyl]phenol provides the corresponding compounds of formula 1: where R is hydrogen or methyl, A is hydroxyl and B is ($C_1$-$C_4$) alkyl, 7-coumarinyl, phenyl, or phenyl substituted with methoxy, carboxy, carboxymethyl, amino, dimethylamino, hydroxy, or 2-carboxyethenyl.

The compounds of formula 1, where R is hydrogen or ($C_1$-$C_4$) alkyl, A is hydroxyl and B is hydrogen are prepared by treating intermediates of formula 2 with sulfuric acid in tetrahydrofuran.

The compounds of formula 1, where A is chlorine, are prepared by chlorination of the corresponding compound of formula 1, where A is hydroxyl, by treatment with thionyl chloride in an inert solvent and in the particular cases where B is hydrogen by treatment of the intermediate of formula 2, with hydrochloric acid in tetrahydrofuran.

The compounds of formula 1 where B is phosphono are prepared from the corresponding compounds of formula 1 where B is hydroxyl by reaction with diphenylchlorophosphate in the presence of pyridine followed by catalytic hydrogenation.

Some of the compounds of formula 1 do not contain acidic or basic functional groups and therefore no salt forms can be prepared for these compounds. However, many of the compounds of general formula 1 do contain acid or basic groups and various pharmaceutically acceptable salt forms may be prepared. Acid addition salts are prepared from the compounds of formula 1 containing basic groups by treatment with mineral or organic acids such as hydrochloric, hydrobromic, sulfuric, phosphoric, acetic, lactic, maleic, fumaric, citric, tartaric, succinic, methanesulfonic or toluenesulfonic acids and the like. Base addition salts are prepared from the compounds of formula 1 containing acidic groups by treatment with inorganic bases such as lithium, sodium, potassium, calcium, barium, aluminium, or magnesium hydroxides and the like; or with organic bases such as ammonia, methylamine, 2-aminoethanol, 2-(dimethylamino) ethanol, ethylenediamine, cyclohexylamine, and the like.

The antihypoxia activity of the compounds of this invention was determined by a study of their ability to protect mice from death due to the lack of oxygen in an environmental chamber flush with a 96% nitrogen/4% oxygen atmosphere, a condition resulting in normobaric hypoxia. The time to death of groups of 5 or more treated mice were statistically compared with matched groups of untreated mice and the minimum active does (MAD) and/or the dose which produced a 100% increase in survival time (100%S) was determined. The compounds of formula 1 demonstrated activity in these studies at MAD's usually ranging from 0.1–400 mg/kg and at 100%S's usually ranging from 14–400 mg/kg depending on the compound and route of administration. Activity was observed after intraperitoneal, oral or intravenous dosing.

The following specific non-limiting procedures and examples are provided to illustrate the preparation of intermediates and of the various compounds of the invention wherein percents are percent by volume unless otherwise indicated.

PREPARATION OF INTERMEDIATES

Procedure 1

Preparation of 7,8,9,10-tetrahydro-3-methyl-1-(oxiranylmethoxy)-6-oxo-6H-dibenzo[b,d]pyran To a stirred solution of NaOH (4.0 g. 0.1 mol) in dimethylsulfoxide (DMSO) (250 ml) and water (250 ml), was added 7,8,9,10-tetrahydro-1-hydroxy-3-methyl-6-oxo-6H-dibenzo[b,d]pyran (20.0 g. 0.087 mol) and the mixture stirred for 5 minutes, then treated with epichlorohydrin (50 ml). After 5 hours the mixture was cooled in a ice bath for 30 minutes and the precipitated solid collected by filtration, washed with water and dried to give 7,8,9,10-tetrahydro-3-methyl-1-(oxiranylmethoxy)-6-oxo-6H-dibenzo[b,d]pyran as a white solid, m.p. 164°–165° C. An analytical sample recrystallized from methanol melted at 165°–166° C.

Procedure 2

Preparation of 7,8,9,10-tetrahydro-3-(oxiranylmethoxy)-6-oxo-6H-dibenzo[b,d]pyran To a stirred solution of NaOH (2.0 g, 0.05 mol) in DMSO (125 ml) and water (125 ml) was added 7,8,9,10-tetrahydro-3-hydroxy-6-oxo-6H-dibenzo[b,d]pyran (10.0 g, 0.045 mol). When a solution was obtained, the mixture was treated with epichlorohydrin (35 ml) and stirred for 56 hours. A white solid precipitated which was collected by filtration to give 12.1 g of a mixture consisting of ca. 90% 7,8,9,10-tetrahydro-3-(oxiranylmethoxy)-6-oxo-6H-dibenzo[b,d]pyran. The pure epoxide was obtained by chromatography on SiO$_2$ and crystallization from 300 ml of methanol/chloroform (6/1) gave 8.0 g of white solid, mp. 120°–121° C.

EXAMPLES

Example 1

Preparation of 3-(7,8,9,10-tetrahydro-6-oxo-dibenzo[b,d]pyranoxy)-1-methoxy-2-propanol To a stirred solution of sodium hydroxide (1.6 g, 0.04 mol) in 300 ml of methanol and 50 ml of water was added 7,8,9,10-tetrahydro-3-(oxiranylmethoxy)-6-oxo-6H-dibenzo[b,d]pyran (10.88 g, 0.04 mol) and the mixture heated on a steam bath for 55 min., then allowed to cool and stir for 16 hrs. The solvent was evaporated, the residue dissolved in 800 ml of chloroform, washed with water (500 ml), and dried over MgSO$_4$. Evaporation of the solvent gave an oily residue which was purified by chromatography on SiO$_2$, eluting with 0.1% CH$_3$OH/CHCl$_3$, to give 8.0 g of a white solid. This was recrystallized from a mixture of 100 ml of cyclohexane and 10 ml of chloroform and vacuum dried at 60° C. for 48 hrs to give 7.3 g of 3-(7,8,9,10-tetrahydro-6-oxo-6H-dibenzo [b,d]pyranyl-3-oxy)-1-methoxy-2-propanol, mp. 110°–111° C.

Example 2

Preparation of 3-(7,8,9,10-tetrahydro-6-oxo-6H-dibenzo[b,d]pyranyl-3-oxy)-1-ethoxy-2-propanol To a stirred solution of sodium hydroxide (1.6 g, 0.04 mol) in 200 ml of ethanol and 50 ml of water was added 7,8,9,10-tetrahydro-3-(oxiranylmethoxy)-6-oxo-6H-dibenzo[b,d]pyran (10.88 g, 0.04 mol) and the mixture heated to reflux for 1 hr., then allowed to cool and stir for 16 hrs. The solvent was evaporated and the reside dissolved in 800 ml of chloroform, washed with water (2×500 ml) and dried over MgSO$_4$. Evaporation of the solvent gate an oily residue which was purified by chromatography on SiO$_2$, eluting with 0.5% CH$_3$OH/CHCl$_3$, to give 4.6 g of a white solid. This was recrystallized from a mixture of 10 ml of chloroform and 90 ml of cyclohexane and vacuum dried at 10° C. for 48 hrs to give 3.1 g of 3-(7,8,9,10-tetrahydro-6-oxo-6H-dibenzo[b,d]pyranyl-3-oxy)-1-ethoxy-2-propanol, mp. 91°–92° C.

Using procedures essentially the same as described in Examples 1 and 2 above and substituting n-propanol, i-propanol, n-butanol and t-butanol for methanol or ethanol will provide the corresponding 3-(7,8,9,10-tetrahydro-6-oxo-6H-dibenzo[b,d]pyranyl-3-oxy)-1-(2-propoxy)-2-propanol, 3-(7,8,9,10-tetrahydro-6-oxo-6H-dibenzo[b,d]pyranyl-3-oxy)-1-butoxy-2-propanol and 3-(7,8,9,10-tetrahydro-6-oxo-6H-dibenzo[b,d]pyranyl-3-oxy)-1-[(1,1-dimethyl)ethoxy]-2-propanol, respectively.

Example 3

Preparation of 3-(7,8,9,10-tetrahydro-6-oxo-6H-dibenzo[b,d]pyranyl-3-oxy)-1-(coumarinyl-7-oxy)-2-propanol To a stirred solution of sodium hydroxide (1.2 g, 0.03 mol) in 250 ml of DMSO and 250 ml of water was added at 60° C. 7-hydroxycoumarin (4.86 g, 0.03 mol) and then after 10 min. a solution of 7,8,9,10-tetrahydro-3-(oxiranylmethoxy)-6-oxo-6H-dibenzo[b,d]pyran (9.2 g, 0.034 mol) in 400 ml of DMSO. The mixture was stirred and heated to 75° C. for 26 hours, allowed to cool and then treated with water (1 L), and saturated sodium chloride (1 L) and extracted with ethyl acertate (4×500 ml). The combined extracts were washed with water (1 L), dried over MgSO$_4$, and evaporated to a semisolid residue. This was purified by chromatography on SiO$_2$, eluting with 1% CH$_3$OH/CHCl$_3$, to give 3.2 g of a pure white solid material which was recrystallized from a mixture of 150 ml of methanol and 5 ml of chloroform and vacuum dried at 85° C. for 24 hrs, providing 2.2 g of 3-(7,8,9,10-tetrahydro-6-oxo-6H-dibenzo[b,d]pyranyl-3-oxy)-1-(coumarinyl-7-oxy)-2-propanol, mp. 162°–164° C.

Example 4

Preparation of 3-(7,8,9,10-tetrahydro-6-oxo-6H-dibenzo[b,d]pyranyl-3-oxy)-1-(3-methoxyphenoxy)-2-propanol To a stirred solution of sodium hydroxide (1.2 g, 0.03 mol) in 100 ml of ethanol and 50 ml of water was added 3-methoxyphenol (3.72 g, 0.03 mol) and then a solution of 7,8,9,10-tetrahydro-3-(oxiranylmethoxy)-6-oxo-6H-dibenzo[b,d]pyran (10.0 g, 0.0367 mol) in 300 ml of ethanol and the mixture stirred for 24 hours. The solvent was evaporated and the residue dissolved in 500 ml of chloroform and washed with 5% by weight NaOH (2×50 ml), water (500 ml) and dried over MgSO$_4$. Evaporation of the solvent gave an oily residue which was purified by chromatography on SiO$_2$, eluting with 0.5% CH$_3$OH/CHCl$_3$, crystallized from 200 ml of petroleum ether, and vacuum dried at 55° C. for 24 hrs. to give 2.8 g of 3-(7,8,9,10-tetrahydro-6-oxo-6H-dibenzo[b,d]pyranyl-3-oxy)-1-(3-methoxyphenoxy)-2-propanol, mp. 85°–86° C.

Using procedures essentially the same as outlined above and substituting phenol, 2-methoxyphenol or 4-methoxyphenol for 3-methoxyphenol, will provide the corresponding 3-(7,8,9,10-tetrahydro-6-oxo-6H-dibenzo[b,d]pyranyl-3-oxy)-1-phenoxy-2-propanol, 3-(7,8,9,10-tetrahydro-6-oxo-6H-dibenzo[b,d]pyranyl-3-oxy)-1-(2-methoxyphenoxy)-2-propanol, and 3-(7,8,9,10-tetrahydro-6-oxo-6H-dibenzo[b,d]pyranyl-3-oxy)-1-(4-methoxyphenoxy)-2-propanol, respectively.

Example 5

Preparation of 3-(7,8,9,10-tetrahydro-6-oxo-6H-dibenzo[b,d]pyranyl-3-oxy)-1-(3-carboxyphenoxy)-2-propanol To a stirred solution of sodium hydroxide (3.2 g, 0.08 mol) in 300 ml of DMSO and 100 ml of water was added 3-hydroxybenzoic acid (5.52 g, 0.04 mol) and then 7,8,9,10-tetrahydro-3-(oxiranylmethoxy)-6-oxo-6H-dibenzo[b,d]pyran (10.88 g, 0.04 mol) and the mixture heated to 65°–70° C. for 5 hrs, then cooled and poured into 1 L of water. The mixture was acidified to pH 1 with conc. HCl, extracted with chloroform (3 × 500 ml), and the extracts washed with 2 × 500 ml of 5% HCl then dried over $MgSO_4$. The solvent was evaporated and the solid residue purified by chromatography on $SiO_2$, eluting with 1% $CH_3OH/CHCl_3$ to give 8.1 g of an off-white solid. This was recrystallized from a mixture of 125 ml of methanol and 25 ml of ethylacetate and vacuum dried at 85° C. for 24 hrs to give 4.4 g of 3-(7,8,9,10-tetrahydro-6-oxo-6H-dibenzo[b,d]pyranyl-3-oxy)-1-(3-carboxyphenoxy)-2-propanol, mp. 186°–187° C.

Example 6

Preparation of 3-(7,8,9,10-tetrahydro-6-oxo-6H-dibenzo[b,d]pyranyl-3-oxy)-1-(4-carboxyphenoxy)-2-propanol To a stirred solution of sodium hydroxide (3.2 g, 0.08 mol) in 300 ml of DMSO and 100 ml of water was added 4-hydroxybenzoic acid (5.52 g, 0.04 mol) and then 7,8,9,10-tetrahydro-3-(oxiranylmethoxy)-6-oxo-6H-dibenzo[b,d]pyran (10.88 g, 0.04 mol) and mixture heated to 75° C. for 3 hrs, allowed to cool and stir for 16 hrs, then poured into 1 L of water. The mixture was acidified to pH 1 with conc. HCl, extracted with chloroform (3 × 500 ml), the extracts washed with 2 × 500 ml of 5% HCl, extracted with chloroform (3 × 500 ml), the extracts washed with 2 × 500 ml of 5% HCL, and dried over $MgSO_4$. The solvent was evaporated and the residue purified by chromatography on $SiO_2$, eluting with 0.1% $CH_3OH/0.5\%$ acetic acide/$CHCl_3$, to give a solid which was recrystallized from methanol and vacuum dried for 85 hrs at 65° C. to give 1.91 g of 3-(7,8,9,10-tetrahydro-6-oxo-6H-dibenzo[b,d]pyranyl-3-oxy)-1-(4-carboxyphenoxy)-2-propanol, mp. 190°–191° C.

Using a procedure essentially the same as described above and substituting 2-hydroxybenzoic acid for 4-hydroxybenzoic acid will provide the corresponding 3-(7,8,9,10-tetrahydro-6-oxo-6H-dibenzo[b,d]pyranyl-3-oxy)-1-(2-carboxyphenoxy)-2-propanol.

Example 7

Preparation of 3-(7,8,9,10-tetrahydro-6-oxo-6H-dibenzo[b,d]pyranyl-3-oxy)-1-[4-(carboxymethyl)phenoxy]-2-propanol To a stirred solution of sodium hydroxide (2.9 g, 0.072 mol) in 300 ml of DMSO and 100 ml of water was added (4-hydroxyphenyl)acetic acid (5.6 g, 0.036 mol) and then 7,8,9,10-tetrahydro-3-(oxiranylmethoxy)-6-oxo-6H-dibenzo]b,d]pyran (10.0 g, 0.036 mol) and the mixture heated to 75° C. for 3 hrs, allowed to cool and stir for 16 hrs, then poured in 1 L of water. The mixture was acidified to pH 1 with conc. HCl, extracted with chloroform (3 × 500 ml), the extracts washed with 2 × 500 ml of 5% HCl and dried over $MgSO_4$. The solvent was evaporated and the residue purified by chromatography on $SiO_2$, eluting with 2.5% $CH_3OH/0.5\%$ acetic acid/$CHCl_3$, and recrystallized from first 100 ml of ethanol and then from a mixture of 100 ml of isopropanol and 5 ml of methanol and vacuum dried at 70° C. for 72 hrs to give 2.7 g of 3-(7,8,9,10-tetrahydro-6-oxo-6H-dibenzo[b,d]pyranyl-3-oxy)-1-[4-(carboxymethyl)phenoxy]-2-propanol, mp. 139.5°–140.5° C.

Utilizing procedures essentially the same as that described above and substituting (2-hydroxyphenyl)acetic acid or (3-hydroxyphenyl)acetic acid for (4-hydroxyphenyl)acetic acid will provide the corresponding 3-(7,8,9,10-tetrahydro-6-oxo-6H-dibenzo[b,d]pyranyl-3-oxy)-1-[2-(carboxymethyl)phenoxy]-1-propanol and 3-(7,8,9,10-tetrahydro-6-oxo-6H-dibenzo[b,d]pyranyl-3-oxy)-1-[3-(carboxymethyl)phenoxy]-2-propanol, respectively.

Example 8

Preparation of 3-(7,8,9,10-tetrahydro-6-oxo-6H-dibenzo[b,d]pyranyl-3-oxy)-1-(3-aminophenoxy)-2-propanol hydrochloride To a stirred solution of sodium hydroxide (2.2 g, 0.054 mol) in 400 ml of DMSO and 100 ml of water was added 3-aminophenol (5.5 g, 0.054 mol) and then 7,8,9,10-tetrahydro-3-(oxiranylmethoxy)-6-oxo-6H-dibenzo[b,d]pyran (15.0 g, 0.054 mol) and the mixture heated to 40° C. for 3 hrs, stirred at ambient temperature for 4 days, then poured into 1 L of water. The mixture was extracted with 3 × 500 ml of chloroform and the extracts washed with 2 × 500 ml of water, 500 ml of brine and dried over $MgSO_4$. The solvent was evaporated and the residue purified by chromatography on $SiO_2$, eluting with 25% ethylacetate/1% diethylamine/$CHCl_3$, to give 7.8 g of pure base. This was converted to the salt by treatment with HCl gas in 150 ml of ethanol and crystallization. Vacuum drying at 80°–90° C. for 4 days gave 5.8 g of 3-(7,8,9,10-tetrahydro-6-oxo-6H-dibenzo[b,d]pyranyl-3-oxy)-1-(3-aminophenoxy)-2-propanol hydrochloride mp. 214°–215° C.

Utilizing procedures essentially the same as that described above and substituting 2-aminophenol or 4-aminophenol for 3-aminophenol will provide the corresponding 3-(7,8,9,10-tetrahydro-6-oxo-6H-dibenzo[b,d]pyranyl-3-oxy)-1-(2-aminophenoxy)-2-propanol hydrochloride and 3-(7,8,9,10-tetrahydro-6-oxo-6H-dibenzo[b,d]pyranyl-3-oxy)-1-(4-aminophenoxy)-2-propanol hydrochloride, respectively.

Example 9

Preparation of
3-(7,8,9,10-tetrahydro-6-oxo-6H-dibenzo[b,d]pyranyl-3-oxy)-1-[3-(dimethylamino)phenoxy]-2-propanol hydrochloride To a stirred solution of sodium hydroxide (1.5 g, 0.036 mol) in 300 ml of DMSO and 60 ml of water was added 3-(dimethylamino)phenol (5.0 g, 0.036 mol) and then 7,8,9,10-tetrahydro-3-(oxiranylmethoxy)-6-oxo-6H-dibenzo[b,d]pyran (9.3 g, 0.034 mol). The mixture was stirred for 2 days and then poured in 1 L of water. The mixture was extracted with chloroform (3×500 ml) and the extracts washed with 2×500 ml of 5% by weight NaOH and dried over MgSO4. The solvent was evaporated and the residue purified by chromatography on SiO2, eluting with 10% ethyl acetate/chloroform and again eluting with chloroform, to give the pure amine base. This was converted to the hydrochloride salt by treatment with HCl gas in 150 ml of ethanol and crytallization. Vacuum drying at 90° C. for 40 hrs. provided 3.9 g of 3-(7,8,9,10-tetrahydro-6-oxo-6H-dibenzo[b,d]pyranyl-3-oxy)-1-[3-(dimethylamino)phenoxy]-2-propanolhydrochloride as a white solid, mp. 197.5°–198.5° C.

Utilizing procedures essentially the same as that described above and substituting 2-(dimethylamino)phenol or 4-(dimethylamino)phenol for 3-(dimethylamino)phenol will provide the corresponding 3-(7,8,9,10-tetrahydro-6-oxo-6H-dibenzo[b,d]pyranyl-3-oxy)-1-[2-dimethylamino)phenoxy]-2-propanol hydrochloride and 3-(7,8,9,10-tetrahydro-6-oxo-6H-dibenzo[b,d]pyranyl-3-oxy)-1-[4-dimethylamino)phenoxy]-2-propanol hydrochloride, respectively.

Example 10

Preparation of
cis-3-(7,8,9,10-tetrahydro-6-oxo-6H-dibenzo[b,d]pyranyl-3-oxy)-1-[4-(2-carboxyethenyl)phenoxy]-2-propanol To a stirred solution of sodium hydroxide (3.28 g, 0.082 mol) in 400 ml of DMSO and 100 ml of water was added cis-4-hydroxycinnamic acid (6.7 g, 0.041 mol) and then a solution of 7,8,9,10-tetrahydro-3-(oxiranylmethoxy)-6-oxo-6H-dibenzo[b,d]pyran (11.17 g, 0.041 mol) in 100 ml of DMSO, and the mixture heated to 50° C. for 72 hrs., cooled, and poured into 1 L of water. The mixture was acidified to pH 1 with conc. HCl, extracted with 3×500 ml of chloroform and the extracts washed with 2×300 ml of 5% HCl and dried over MgSO4. The solvent was evaporated and the residue purified by chromatography on SiO2, eluting with chloroform and again eluting with 5% CHCl3/toluene, to give a white solid, 7.0 g, which was recrystallized from a mixture of ethylacetate (100 ml) and toluene (100 ml) and vacuum dried at 90° for 72 hrs. to give 4.3 g of cis-3-(7,8,9,10-tetrahydro-6-oxo-6H-dibenzo[b,d]pyranyl-3-oxy)-1-[4-(2-carboxyethenyl)phenoxy]-2-propanol; mp. 149°–151° C.

Utilizing procedures essentially identical to that described above and subtituting cis-2-hydroxycinnamic acid or cis-3-hydroxycinnamic acid for cis-4-hydroxycinnamic acid will provide the corresponding cis-3-(7,8,9,10-tetrahydro-6-oxo-6H-dibenzo[b,d]pyranyl-3-oxy)-1-[2-(2-carboxyethenyl)phenoxy]-2-propanol and cis-3-(7,8,9,10-tetrahydro-6-oxo-6H-dibenzo[b,d]pyranyl-3-oxy)-1-[3-(2-carboxyethenyl)phenoxy]-2-propanol, respectively.

Example 11

Preparation of
trans-3-(7,8,9,10-tetrahydro-6-oxo-6H-dibenzo[b,d]pyranyl-3-oxy)-1-[4-(2-carboxyethenyl)phenoxy]-2-propanol To a stirred solution of sodium hydroxide (3.52 g, 0.088 mol) in 430 ml of DMSO and 100 ml of water was added trans-4-hydroxycinnamic acid (7.26 g, 0.044 mol) and then a solution of 7,8,9,10-tetrahydro-3-(oxiranylmethoxy)-6-oxodibenzo[b,d]pyran (12.1 g, 0.044 mol) and the mixture heated to 40° C. for 22 hrs., cooled to ambient temperature and stirred for 72 hrs., then poured into 400 ml of water. The mixture was acidified to pH 1 with 5% HCl, extracted with 2×800 ml of chloroform, the extracts washed with 2×500 ml of 5% HCl and dried over MgSO4. The solvent was evaporated and the oily residue purified by chromatography on SiO2, eluting with 5% CH3OH/toluene, and recrystallized from a mixture of 50 ml of toluene and 50 ml of isopropanol and then from 100 ml of ethanol and vacuum dried at 70° C. for 72 hrs. to give 3.46 g of trans-3-(7,8,9,10-tetrahydro-6-oxo-6H-dibenzo[b,d]pyranyl-3-oxy)-1-[4-(2-carboxyethenyl)phenoxy]-2-propanol, mp. 200°–201° C.

Utilizing procedures essentially the same as described above and substituting trans-2-hydroxycinnamic acid or trans-3-hydroxycinnamic acid for trans-4-hydroxycinnamic acid will provide the corresponding trans-3-(7,8,9,10-tetrahydro-6-oxo-6H-dibenzo[b,d]pyranyl-3-oxy)-1-[2-(2-carboxyethenyl)phenoxy]-2-propanol and trans-3-(7,8,9,10-tetrahydro-6-oxo-6H-dibenzo[b,d]pyranyl-3-oxy)-1-[3-(2-carboxyethenyl)phenoxy]-2-propanol, respectively.

Example 12

Preparation of
3-(7,8,9,10-tetrahydro-6-oxo-6H-dibenzo[b,d]pyranyl-3-oxy)-1-(3-hydroxyphenoxy)-2-propanol To a stirred solution of sodium hydroxide (23.4 g, 0.584 mol) in 200 ml of DMSO and 100 ml of water was added resorcinol (32.1 g, 0.292 mol), and then a solution of 7,8,9,10-tetrahydro-3-(oxiranylmethoxy)-6-oxo-6H-dibenzo[b,d]pyran (20.0 g, 0.073 mol) in 200 ml of DMSO and the mixture stirred for 72 hrs., then poured into 1 L of water. The mixture was acidified to pH 1 with 20% HCl, extracted with 3×500 ml of chloroform, the extracts washed with 2×500 ml of 5% HCl, dried over MgSO4, and decolorized with Norite. The solvent was evaporated and the residue (37.2 g) purified by chromatography on SiO2, eluting with 2% CH3OH/CHCl3, recrystallized from 100 ml of methanol and vacuum dried at 60° C. for 24 hrs. to give 5.4 g of 3-(7,8,9,10-tetrahydro-6-oxo-6H-dibenzo[b,d]pyranyl-3-oxy)-1-(3-hydroxyphenoxy)-2-propanol, mp. 93°–93° C.

Utilizing procedures essentially the same as described above and substituting 2-hydroxyphenol or 4-hydroxyphenol for 3-hydroxyphenol (resorcinol) will provide the corresponding 3-(7,8,9,10-tetrahydro-6-oxo-6H-dibenzo[b,d]pyranyl-3-oxy)-1-(2-hydroxyphenoxy)-2-propanol and 3-(7,8,9,10-tetrahydro-6-oxo-6H-dibenzo[b,d]pyranol-3-oxy)-1-(4-hydroxyphenoxy)-2-propanol, respectively.

Example 13

Preparation of 3-(7,8,9,10-tetrahydro-3-methyl-6-oxo-6H dibenzo[b,d]pyranyl-1-oxy)-1-(coumarinyl)-7-oxy)-2-propanol To a stirred solution of sodium hydroxide (1.2 g, 0.03 mol) in 100 mol of ethanol and 50 ml of water was added 7-hydroxycoumarin (4.86 g, 0.03 mol) and then a solution of 7,8,9,10-tetrahydro-3-methyl-1-(oxiranylmethoxy)-6-oxo-6H-dibenzo[b,d]pyran (6.3 g, 0.022 mol) in 200 ml ethanol and the mixture stirred for 48 hrs. The solvent was evaporated, the residue dissolved in 500 ml of chloroform and washed with 500 ml of 1% by weight NaOH, 500 ml of water and dried over $MgSO_4$. The solvent was evaporated to a solid residue (8.6 g) which was purified by chromatography on $SiO_2$, eluting with 2% $CH_3OH/CHCl_3$, and vacuum dried at 90° for 24 hrs. to give 1.6 g of 3-(7,8,9,10-tetrahydro-3-methyl-6-oxo-6H-dibenzo[b,d]pyranyl-1-oxy)-1-(coumarinyl-7-oxy)-2-propanol, mp. 210°–211° C.

Example 14

Preparation of 3-(7,8,9,10-tetrahydro-3-methyl-6-oxo-6H-dibenzo[b,d]pyranyl-1-oxy)-1-substituted-2-propanols Utilizing procedures seentially the same as described in examples 1–12 and as in Example 13 substituting 7,8,9,10-tetrahydro-3-methyl-1-(oxiranylmethoxy)-6-oxo-6H-dibenzo[b,d]pyran for 7,8,9,10-tetrahydro-3-(oxiranylmethoxy)-6-oxo-6H-dibenzo[b,d]pyran, will provide the corresponding isomeric 3-(7,8,9,10-tetrahydro-3-methyl-6-oxo-6H-dibenzo[b,d]pyranyl-1-oxy)-1-substituted-2-propanols.

Example 15

Preparation of 3-(7,8,9,10-tetrahydro-6-oxo-6H-dibenzo[b,d]pyranyl-3-oxy)-1-hydroxy-2-propanol A stirred suspension of 7,8,9,10-tetrahydro-3-(oxiranylmethoxy)-6-oxo-6H-dibenzo[b,d]pyran (20 g., 0.069 mol) in tetrahydrofuran (0.6 L) was cooled to 5° C. and treated with a solution of 98% $H_2SO_4$ (15 ml) and water (25 ml). The cooling bath was removed and the mixture stirred for 30 min. then quenched with the addition of 300 ml water and 400 ml of brine. Extraction with ether, washing with $KHCO_3$, drying over $MgSO_4$ and evaporation of the solvent gave a white semisolid residue. This material was purified by chromatography on silica gel, recrystallized from ethylacetate and vacuum dried at 70° C. for 6 hrs. to give 3-(7,8,9,10-tetrahydro-6-oxo-6H-dibenzo[b,d]pyranyl-3-oxy)-1-hydroxy-2-propanol 5.0 g was a white solid, mp. 132°–133° C.

Example 16

Preparation of 3-(7,8,9,10-tetrahydro-3-methyl-6-oxo-6H dibenzo[b,d]pyranyl-1-oxy)-1-hydroxy-2-propanol Utilizing the procedure described in Example 15 and substituting 7,8,9,10-tetrahydro-3-methyl-1-(oxiranylmethoxy)-6-oxo-6H-dibenzo[b,d]pyran for 7,8,9,10-tetrahydro-3-(oxiranylmethoxy)-6-oxo-6H-dibenzo[b,d]pyran, the corresponding 3-(7,8,9,10-tetrahydro-3-methyl-6-oxo-6H-dibenzo[b,d]pyranyl-1-oxy)-1-hydroxy-2-propanol is obtained as a white solid, mp. 145°–146° C.

Example 17

Preparation of 3-(7,8,9,10-tetrahydro-3-methyl-6-oxo-6H-dibenzo[b,d]pyranyl-1-oxy)-1-hydroxy-2-chloropropane A stirred suspension of 7,8,9,10-tetrahydro-3-methyl-1-(oxiranylmethoxy)-6-oxo-6H-dibenzo[b,d]pyran (5.0 g, 0.0175 mol) in tetrahydrofuran was treated with 10 ml of 10% HCl. After 30 min., the solvent was evaporated and the residue dissolved in chloroform (200 ml), washed with water (3×200 ml) and dried over $MgSO_4$. Evaporation of the solvent gave an oil that solidified on standing. Recrystallization from 60 ml of 3:1 by volume ethylacetate:cyclohexane gave 3.32 g of 3-(7,8,9,10-tetrahydro-3-methyl-6-oxo-6H-dibenzo[b,d]pyranyl-1-oxy)-1-hydroxy-2-chloropropane as a white solid, mp. 108°–110° C.

Example 18

Preparation of 3-(7,8,9,10-tetrahydro-3-methyl-oxo-6H-dibenzo[b,d]pyranyl-1-oxy)-2-chloro-1-propanol dihydrogen phosphate cyclohexylamine salt A solution of 3-(7,8,9,10-tetrahydro-3-methyl-6-oxo-6H-dibenzo[b,d]pyranyl-1-oxy)-1-hydroxy-2-chloropropane (9.1 g, 0.03 mol) in 200 ml of anhydrous pyridine at 0° C. was treated with diphenylchlorophosphate (9.0 g, 0.034 mol) and the mixture maintained at 0° C. for 96 hrs. Water (5 ml) was added and the pyridine evaporated to an oily residue which was dissolved in chloroform (500 ml) and washed with 2×400 ml cold 2% HCl, 400 ml cold 2% by weight $KHCO_3$, 400 ml water, and dried over $MgSO_4$. The solvent was evaporated to an oil which was dissolved in 500 ml absolute ethanol and hydrogenated at 40 psi over 1.0 g. Pt catalyst for 5 hours. The catalyst was removed by filtration and the filtrate treated with 8.0 g cyclohexylamine and the salt allowed to crystallize at 0° C. to give 12.5 g of the crude cyclohexylamine salt. Recrystallization from 2:1 by volume methanol:acetone (150 ml) gave 7.44 g of 3-(7,8,9,10-tetrahydro-3-methyl-6-oxo-6H-dibenzo[b,d]pyranyl-1-oxy)-2-chloro-1-propanol dihydrogen phosphate cyclohexylamine salt, mp. 170°–173° C.

I claim:

1. A compound having the formula:

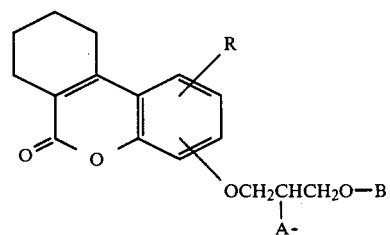

where R represents hydrogen or $(C_1–C_4)$alkyl: where A represents chlorine or hydroxyl; and where B represents, hydrogen $(C_1–C_4)$alkyl, 7-coumarinyl, phosphono, phenyl, or phenyl substituted with amino, dimethylamino, hydroxyl, methoxyl, carboxyl, carboxymethyl, or 2-carboxyethenyl (HOOC—CH=CH—) provided that when A is hydroxyl, B can not be hydrogen.

2. A compound according to claim 1 which contains an acid group.

3. A base addition salt of the compound according to claim 2.

4. A compound according to claim 1 which contains a basic group.

5. An acid addition salt of the compound according to claim 4.

6. A compound according to claim 1 where A is hydroxyl and B is other than hydrogen.

7. A compound according to claim 1 wherein A is chlorine.

8. A compound according to claim 1 wherein the compound is 3-(7,8,9,10-tetrahydro-6-oxo-6H-dibenzo[b,d]pyranyl-3-oxy)-1-methoxy-2-propanol.

9. A compound according to claim 1 wherein the compound is 3-(7,8,9,10-tetrahydro-3-methyl-6-oxo-6H-dibenzo[b,d]pyranyl-1-oxy)-1-hydroxy-2-chloropropane.

10. A compound according to claim 1 wherein the compound is 3-(7,8,9,10-tetrahydro-6-oxo-6H-dibenzo[b,d]pyranyl-3-oxy)-1-ethoxy-2-propanol.

11. A compound according to claim 1 wherein the compound is 3-(7,8,9,10-tetrahydro-6-oxo-6H-dibenzo[b,d]pyranyl-3-oxy)-1-(coumarinyl-7-oxy)-2-propanol.

12. A compound according to claim 1 wherein the compound is 3-(7,8,9,10-tetrahydro-6-oxo-6H-dibenzo[b,d]pyranyl-3-oxy)-1-(3-methoxyphenoxy)-2-propanol.

13. A compound according to claim 1 wherein the compound is 3-(7,8,9,10-tetrahydro-6-oxo-6H-dibenzo[b,d]pyranyl-3-oxy)-1-(3-carboxyphenoxy)-2-propanol.

14. A compound according to claim 1 wherein the compound is 3-(7,8,9,10-tetrahydro-6-oxo-6H-dibenzo[b,d]pyranyl-3-oxy)-1-(4-carboxyphenoxy)-2-propanol.

15. A compound according to claim 1 wherein the compound is 3-(7,8,9,10-tetrahydro-6-oxo-6H-dibenzo[b,d]pyranyl-3-oxy)-1-[4-(carboxymethyl)phenoxy]-2-propanol.

16. A compound according to claim 1 wherein the compound is cis-3-(7,8,9,10-tetrahydro-6-oxo-6H-dibenzo[b,d]pyranyl-3-oxy)-1-[4-(2-carboxyethenyl)phenoxy]-2-propanol.

17. A compound according to claim 1 wherein the compound is trans-3-(7,8,9,10-tetrahydro-6-oxo-6H-dibenzo[b,d]pyranyl-3-oxy)-1-[4-(2-carboxyethenyl)phenoxy]-2-propanol.

18. A compound according to claim 1 wherein the compound is 3-(7,8,9,10-tetrahydro-6-oxo-6H-dibenzo[b,d]pyranyl-3-oxy)-1-(3-hydroxyphenoxy)-2-propanol.

19. A compound according to claim 1 wherein the compound is 3-(7,8,9,10-tetrahydro-3-methyl-6-oxo-6H-dibenzo[b,d]pyranyl-1-oxy)-1-(coumarinyl-7-oxy)-2-propanol.

20. A compound according to claim 5 wherein the compound is 3-(7,8,9,10-tetrahydro-6-oxo-6H-dibenzo[b,d]pyranyl-3-oxy)-1-(3-aminophenoxy)-2-propanol hydrochloride.

21. A compound according to claim 5 wherein the compound is 3-(7,8,9,10-tetrahydro-6-oxo-6H-dibenzo[b,d]pyranyl-3-oxy)-1-[3-(dimethylamino)phenoxy]-2-propanol hydrochloride.

22. A compound according to claim 3 wherein the compound is 3-(7,8,9,10-tetrahydro-3-methyl-oxo-6H-dibenzo[b,d]pyranyl-1-oxy)-2-chloro-1-propanol dihydrogen phosphate cyclohexylamine salt.

* * * * *